United States Patent [19]
Jacobs et al.

[11] Patent Number: 6,043,344
[45] Date of Patent: Mar. 28, 2000

[54] HUMAN CTLA-8 AND USES OF CTLA-8-RELATED PROTEINS

[75] Inventors: Kenneth Jacobs, Newton; Kerry Kelleher, Marlborough; McKeough Carlin, Cambridge; Samuel Goldman, Acton, all of Mass.; Debra Pittman, Windham, N.H.; Sha Mi, Belmont, Mass.; Steven Neben; Joanne Giannotti, both of Acton, Mass.; Margaret M. Golden-Fleet, Medford, Mass.

[73] Assignee: Genetics Institute, Inc., Cambridge, Mass.

[21] Appl. No.: 09/034,810

[22] Filed: Mar. 4, 1998

Related U.S. Application Data

[60] Division of application No. 08/685,239, Jul. 18, 1996, abandoned, which is a continuation-in-part of application No. 08/504,032, Jul. 19, 1995, which is a continuation-in-part of application No. 08/514,014, Aug. 11, 1995, Pat. No. 5,707,829
[60] Provisional application No. 60/035,347, Jul. 19, 1995.

[51] Int. Cl.$^7$ .................................................. C07K 14/54
[52] U.S. Cl. ........................ 530/351; 530/350; 424/85.1
[58] Field of Search ................................. 530/351, 350; 424/85.1

[56] References Cited

FOREIGN PATENT DOCUMENTS 9518826  7/1995  WIPO.

OTHER PUBLICATIONS

Rouvier et al, *J. Immunol*, 150, 1993, p. 5445–556.
Yao et al., *J. Immunol* 155 (12) 1995, p. 5483–486.
Nicholas et al., Virology 179, 1990, p. 189–200.

*Primary Examiner*—Garnette D. Draper
*Attorney, Agent, or Firm*—Lahive & Cockfield, LLP; Amy E. Mandragouras, Esq.; Peter C. Lauro, Esq.

[57] ABSTRACT

Polynucleotides encoding human CTLA-8 and related proteins are disclosed. Human CTLA-8 proteins and methods for their production are also disclosed. Methods of treatment using human CTLA-8 proteins, rat CTLA-8 proteins and herpesvirus herpes CTLA-8 proteins are also provided.

13 Claims, 7 Drawing Sheets

Fig. 1

HUMAN CTLA-8 AND USES OF CTLA-8-RELATED PROTEINS

This application is a divisional of application Ser. No. 08/685,239, filed Jul. 18, 1996, now abandoned, which is a continuation-in-part of application of Ser. No 08/504,032 filed Jul. 19, 1995, now converted to Provisional application No. 60/035347 filed Jul. 19, 1995, and a continuation-in-part of application Ser. No. 08/514,014, filed Aug. 11, 1995, now U.S. Pat. No. 5,707,829.

FIELD OF THE INVENTION

The present invention relates to human CTLA-8 proteins, nucleic acids encoding such proteins, methods of treatment using such proteins. The invention also relates to the use of rat CTLA-8 proteins and herpesvirus Saimiri ORF13 proteins in methods of treatment.

BACKGROUND OF THE INVENTION

Cytokines are secreted proteins which act on specific hematopoietic target cells to cause a differentiation event or on other target cells to induce a particular physiological response, such as secretion of proteins characteristic of inflammation. Cytokines, also variously known as lymphokines, hematopoietins, interleukins, colony stimulating factors, and the like, can be important therapeutic agents, especially for diseases or conditions in which a specific cell population is depleted. For example, erythropoietin, G-CSF, and GM-CSF, have all become important for treatment of anemia and leukopenia, respectively. Other cytokines such as interleukin-3, interleukin-6, interleukin-11 and interleukin-12 show promise in treatment of conditions such as thrombocytopenia and modulation of immune response.

For these reasons a significant research effort has been expended in searching for novel cytokines and cloning the DNAs which encode them. In the past, novel cytokines were identified by assaying a particular cell such as a bone marrow cell, for a measurable response, such as proliferation. The search for novel cytokines has thus been limited by the assays available, and if a novel cytokine has an activity which is unmeasurable by a known assay, the cytokine remains undetectable. In a newer approach, cDNAs encoding cytokines have been detected using the polymerase chain reaction (PCR) and oligonucleotide primers having homology to shared motifs of known cytokines or their receptors. The PCR approach is also limited by the necessity for knowledge of previously cloned cytokines in the same protein family. Cytokines have also been cloned using subtractive hybridization to construct and screen cDNA libraries, or they can potentially be cloned using PCR followed by gel electrophoresis to detect differentially expressed genes. The subtractive hybridization methods are based on the assumption that cytokine mRNAs are those that are differentially expressed, and these methods do not require any prior knowledge of the sequence of interest. However, many cytokines may be encoded by mRNAs which are not differentially expressed, and thus are undetectable using these methods.

It would be desirable to develop new methods for identifying novel cytokines and other secreted factors and to isolate polynucleotides encoding them.

SUMMARY OF THE INVENTION

In developing the present invention, methods were employed which selectively identify polynucleotides which encode secreted proteins. One such polynucleotide was isolated which encodes "human CTLA-8." In accordance with the present invention, polynucleotides encoding human CILA-8 and active fragments thereof are disclosed. "CTLA-8" is used throughout the present specification to refer to both proteins and polynucleotides encoding those proteins and to refer to proteins and polynucleotides from all mammalian species.

In certain embodiments, the present invention provides an isolated polynucleotide comprising a nucleotide sequence selected from the group consisting of:

(a) the nucleotide sequence of SEQ ID NO: 1 from nucleotide 146 to nucleotide 544;

(b) a nucleotide sequence capable of hybridizing to a nucleic acid sequence specified in (a);

(c) a nucleotide sequence varying from the sequence of the nucleotide sequence specified in (a) as a result of degeneracy of the genetic code; and (d) an allelic variant of the nucleotide sequence specified in (a). Preferably, the polynucleotide of the invention encodes a protein having CTLA-8 activity. In other embodiments the polynucleotide is operably linked to an expression control sequence. In other preferred embodiments, the polynucleotide is contained in a vector suitable for in vivo expression in a mammalian subject. Polynucleotides comprising the nucleotide sequence of SEQ ID NO: 1 from nucleotide 55 to nucleotide 544, the nucleotide sequence of SEQ ID NO: 1 from nucleotide 139 to nucleotide 544 or the nucleotide sequence of SEQ ID NO: 1 from nucleotide 86 to nucleotide 544 are particularly preferred.

Host cells transformed with the polynucleotides of the invention are also provided, including mammalian cells.

Processes are also provided for producing a human CTLA-8 protein, said processes comprising:

(a) growing a culture of the host cell of the invention in a suitable culture medium; and (b) purifying the human CTLA-8 protein from the culture.

Isolated human CTLA-8 protein is also provided which comprising an amino acid sequence selected from the group consisting of:

(a) the amino acid sequence of SEQ ID NO:2;

(b) the amino acid sequence of SEQ ID NO:2 from amino acids 11 to 163;

(c) the amino acid sequence of SEQ ID NO:2 from amino acids 29 to 163;

(d) the amino acid sequence of SEQ ID NO:2 from amino acids 31 to 163; and (e) fragments of (a), (b), (c) or (d) having CTLA-8 activity.

Proteins comprising the amino acid sequence of SEQ ID NO:2 and comprising the sequence from amino acids 29 to 163, from amino acid 31 to 163, or from amino acids 11 to 163 of SEQ ID NO:2 are particularly preferred. Preferably, the protein has CTLA-8 activity. Pharmaceuticals composition comprising a human CTLA-8 protein of the invention and a pharmaceutically acceptable carrier are also provided.

Compositions are also disclosed which comprise an antibody which specifically reacts with a human CTLA-8 protein of the invention.

Methods of treating a mammalian subject are also provided which comprise administering a therapeutically effective amount of a pharmaceutical composition comprising a human CTLA-8 protein.

Rat CTLA-8 and active (i.e., having CTLA-8 activity) fragments thereof may also be used in such methods of treatment. Preferably the rat protein is administered as a composition comprising a pharmaceutically acceptable carrier and a protein comprising an amino acid sequence selected from the group consisting of:

(a) the amino acid sequence of SEQ ID NO:4;
(b) the amino acid sequence of SEQ ID NO:4 from amino acids 18 to 150; and
(c) fragments of (a) or (b) having CTLA-8 activity.

Herpesvirus Saimiri ORF13, referred to herein as "herpes CTLA-8", and active (i.e., having CTLA-8 activity) fragments thereof and active fragments thereof may also be used in such methods of treatment. Preferably the herpes CTLA-8 protein is administered as a composition comprising a pharmaceutically acceptable carrier and a protein comprising an amino acid sequence selected from the group consisting of:

(a) the amino acid sequence of SEQ ID NO:6;
(b) the amino acid sequence of SEQ ID NO:6 from amino acids 19 to 151; and
(c) fragments of (a) or (b) having CTLA-8 activity.

The invention also provides a method of treating a mammalian subject comprising administering a therapeutically effective amount of a composition comprising a pharmaceutically acceptable carrier and IL-17 or an active fragment thereof.

In methods of treatment provided by the present invention, preferably the subject is treated to produce an effect selected from the group consisting of inhibition of angiogenesis, inhibition of growth or proliferation of vascular endothelial cells, inhibition of tumor growth, inhibition of angiogenesis-dependent tissue growth, proliferation of myeloid cells or progenitors, proliferation of erythroid cells or progenitors, proliferation of lymphoid cells or progenitors, induction of IFNγ production, induction of L-3 production and induction of GM-CSF production.

BRIEF DESCRIPTION OF THE FIGURES

Figure 1:
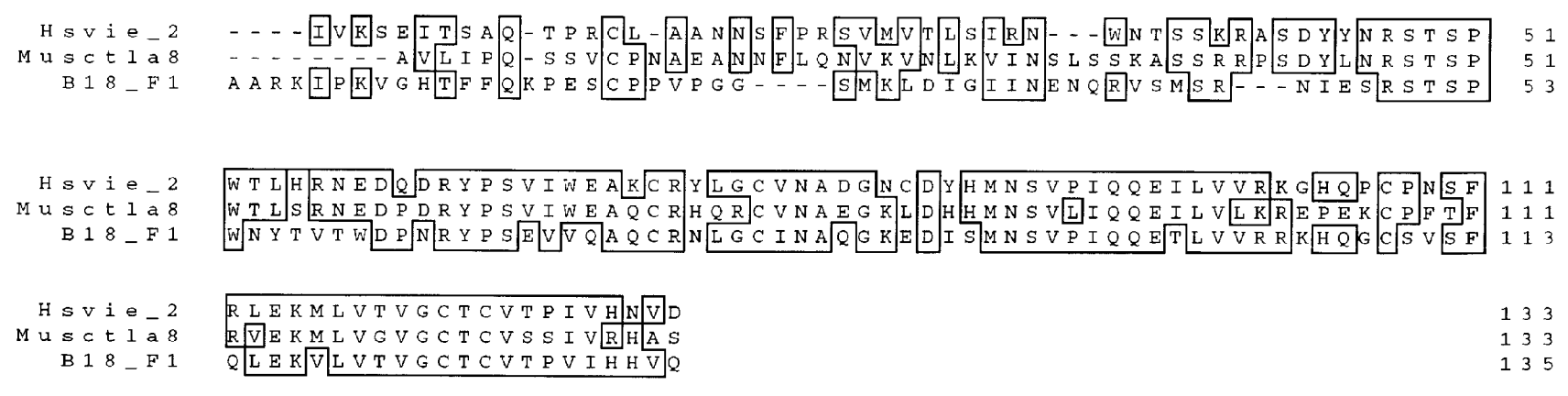

FIG. 1 is a comparison of homologous regions of the amino acid sequences of human CTLA-8 (indicated as "B 18_F1"), rat CTLA-8 (indicated as "Musctla8") and herpes CTLA-8 (indicated as "Hsvie_2").

DETAILED DESCRIPTION OF PREFERRED EMBODIMENTS

Figure 2:
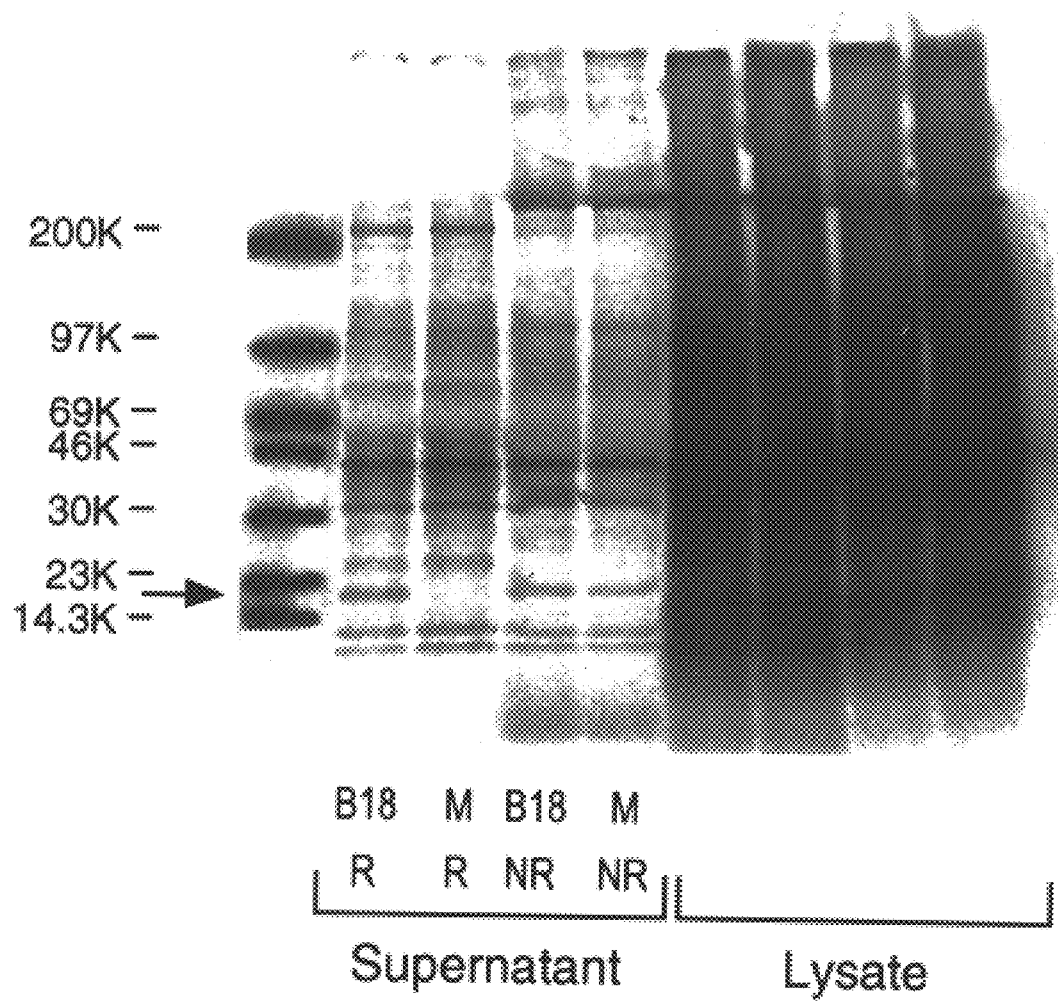
FIG. 2 depicts autoradiographs demonstrating expression of human CTLA-8 in COS cells.

The inventors of the present application have identified and provided a polynucleotide encoding a human CTLA-8 protein. SEQ ID NO:1 provides the nucleotide sequence of a cDNA encoding the human CTLA-8 protein. SEQ ID NO:2 provides the amino acid sequence of the human CTLA-8 protein. Alternatively, the initiating methionine may be at amino acid 11 of SEQ ID NO:2. On the basis of amino terminal sequencing, the mature protein sequence is believed to begin at amino acid 31 of SEQ ID NO:2 (encoded by the sequence beginning with nucleotide 146 of SEQ ID NO: 1).

The region from amino acid 29 to amino acid 163 of human CTLA-8 (SEQ ID NO:2) shows marked homology to portions of rat CTLA-8 (amino acids 18 to 150 of SEQ ID NO:4) and herpesvirus Saimiri ORF13 ("herpes CTLA-8") (amino acids 19 to 151 of SEQ ID NO:6). A cDNA sequence encoding rat CTLA-8 is listed at SEQ ID NO:3 and its corresponding amino acid sequence is reported at SEQ ID NO:4. A cDNA sequence encoding herpes CTLA-8 is listed at SEQ ID NO:5 and its corresponding amino acid sequence is reported at SEQ ID NO:6. Homology between rat CTLA-8 and herpes CTLA-8 was reported by Rouvier et al., J. Immunol. 1993, 150, 5445–5456.

Applicants had previously incorrectly identified the rat sequences of SEQ ID NO:3 and SEQ ID NO:4 as applying to murine CTLA-8. Applicants' human CTLA-8 (B 18) does also show homology to the true murine CTLA-8 sequence.

Golstein et al. (WO95/18826; Fossiez et al., Microbial Evasion and Subversion of Immunity 544:3222 (Abstract)) have also reported a species they initially identified as "human CTLA-8." However, examination of the sequence of the Golstein et al. species and the human CTLA-8 (B18) sequence of the present invention readily reveals that they are two different proteins, although they are homologous with each other and with the rat CTLA-8 and herpes CTLA-8 identified herein. The Golstein et al. species has now been renamed as interleukin-17 (IL-17). Because of the homology between applicants' human CTLA-8 (B118) and IL-17, these proteins are expected to share some activities.

It has also been preliminarily determined that human CTLA-8 (B18) forms homodimers when expressed. As a result, human CTLA-8 proteins may possess activity in either monomeric or dimeric forms. Human CTLA-8 proteins can also be produced as heterodimers with rat and herpes CTLA-8 proteins and with human IL-17. These heterodimers are also expected to have activities of the proteins of which they are comprised.

Forms of human CTLA-8 protein of less than full length are encompassed within the present invention and may be produced by expressing a corresponding fragment of the polynucleotide encoding the human CTLA-8 protein (SEQ ID NO: 1). These corresponding polynucleotide fragments are also part of the present invention. Modified polynucleotides as described above may be made by standard molecular biology techniques, including site-directed mutagenesis methods which are known in the art or by the polymerase chain reaction using appropriate oligonucleotide primers.

For the purposes of the present invention, a protein has "CTLA-8 activity" if it either (1) displays biological activity in a factor-dependent cell proliferation assay (preferably an assay in which full-length the corresponding species full-length CTLA-8 is active) (including without limitation those assays described below), or (2) induces expression or secretion of γ-IFN, or (3) displays chemoattractant or chemotactic activity in a chemoattraction or chemotaxis assay (preferably as assay in which full-length the corresponding species full-length CTLA-8 is active) or (4) induces expression or secretion of IL-3 or GM-CSF.

Human CTLA-8 protein or fragments thereof having CTLA-8 activity may be fused to carrier molecules such as immunoglobulins. For example, human CTLA-8 protein may be fused through "linker" sequences to the Fc portion of an immunoglobulin.

The invention also encompasses allelic variations of the nucleotide sequence as set forth in SEQ ID NO: 1, that is, naturally-occurring alternative forms of the isolated polynucleotide of SEQ ID NO:1 which also encode human CTLA-8 or CTLA-8 proteins having CTLA-8 activity. Also included in the invention are isolated polynucleotides which hybridize to the nucleotide sequence set forth in SEQ ID NO: 1 under highly stringent (0.2xSSC at 65° C.), stringent (e.g. 4xSSC at 65 C or 50% formamide and 4xSSC at 42° C.), or relaxed (4xSSC at 50° C. or 30–40% formamide and 4xSSC at 42° C.) conditions. Isolated polynucleotides which encode human CTLA-8 protein but which differ from the nucleotide sequence set forth in SEQ ID NO:1 by virtue of the degeneracy of the genetic code are also encompassed by the present invention. Variations in the nucleotide sequence as set forth in SEQ ID NO:1 which are caused by point mutations or by induced modifications which enhance CTLA-8 activity, half-life or production level are also included in the invention.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the CTLA-8 protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the CTLA-8 protein is expressed by a host cell which has been transformed (transfected) with the ligated polynucleotide/expression control sequence.

A number of types of cells may act as suitable host cells for expression of the human CTLA-8 protein. Any cell type capable of expressing functional human CTLA-8 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12 or C2C12 cells.

The human CTLA-8 protein may also be produced by operably linking the isolated polynucleotide of the invention to suitable control sequences in one or more insect expression vectors, and employing an insect expression system Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. Soluble forms of the human CTLA-8 protein may also be produced in insect cells using appropriate isolated polynucleotides as described above.

Alternatively, the human CTLA-8 protein may be produced in lower eukaryotes such as yeast or in prokaryotes such as bacteria. Suitable yeast strains include *Saccharomyces cerevisiae, Schizosaccharomyces pombe,* Kluyveromyces strains, Candida, or any yeast strain capable of expressing heterologous proteins. Suitable bacterial strains include *Escherichia coli, Bacillus subtilis, Salmonella typhimurium,* or any bacterial strain capable of expressing heterologous proteins.

The human CTLA-8 protein of the invention may also be expressed as a product of transgenic animals, e.g., as a component of the milk of transgenic cows, goats, pigs, or sheep which are characterized by somatic or germ cells containing a polynucleotide sequence encoding the human CTLA-8 protein.

The human CTLA-8 protein of the invention may be prepared by growing a culture of transformed host cells under culture conditions necessary to express the desired protein. The resulting expressed protein may then be purified from the culture medium or cell extracts. Soluble forms of the human CTLA-8 protein of the invention can be purified from conditioned media. Membrane-bound forms of human CTLA-8 protein of the invention can be purified by preparing a total membrane fraction from the expressing cell and extracting the membranes with a non-ionic detergent such as Triton X-100.

The human CTLA-8 protein can be purified using methods known to those skilled in the art. For example, the human CTLA-8 protein of the invention can be concentrated using a commercially available protein concentration filter, for example, an Amicon or Millipore Pellicon ultrafiltration unit. Following the concentration step, the concentrate can be applied to a purification matrix such as a gel filtration medium Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the human CTLA-8 protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the human CTLA-8 protein. Some or all of the foregoing purification steps, in various combinations or with other known methods, can also be employed to provide a substantially purified isolated recombinant protein.

Preferably, the human CTLA-8 protein is purified so that it is substantially free of other mammalian proteins.

It is believed that human CTLA-8, active fragments and variants thereof, and CTLA-8 related proteins (such as, for example, rat CTLA-8 and herpes CTLA-8) (collectively "CTLA-8 proteins") possess or induce cytokine activities. Human CTLA-8 expression correlated with γ-IFN expression in induced primary cells and can induce the expression of IL-3 and/or GM-CSF, which expression can in turn produce effects associated with the induced cytokine. Therefore, human CTLA-8 and CTLA-8 related proteins may have an effect on proliferation or function of myeloid cells, erythroid cells, lymphoid cells and their progenitors. Human CTLA-8 proteins may also play a role in formation of platelets or their progenitors.

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immnologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E. e.a. Coligan eds. Vol 1 pp. 3.12.1–3.12.14, John Wiley and Sons, Toronto. 1994; and Measurement of mouse and human Interferon γ, Schreiber, R. D. In *Current Protocols in Immunology*. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e.a Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6 - Nordan, R. In *Current Protocols in Immunology*. J. E. e.a Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11 -Bennett, F., Giannotti, J., Clark, S. C. and Turner, K. J. In *Current Protocols in Immunology*. J. E. e.a Coligan eds. Vol 1 pp. 6.15.1 John Wiley and Sons, Toronto. 1991; Measurement of mouse and human Interleukin 9 - Ciarletta, A., Giannotti, J., Clark, S. C. and Turner, K. J. In *Current Protocols in Immunology*. J. E. e.a Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: *Current Protocols in Immunology*, Ed by J. E. Coligan, A. M. Kruisbeek, D. H. Margulies, E. M. Shevach, W Strober Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinbergeret al., Eur. J. Immun. 11:405–411, 1981; Takai et al., J. Immunol. 137:3494–3500, 1986; Takai et al., J. Immunol. 140:508–512, 1988.

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, leshmania, malaria and various fungal infections such as candida. Of course, in this regard, a protein of the present invention may also be useful where a boost to the immune system generally would be indicated, i.e., in the treatment of cancer.

Autoimmune disorders which may be treated using a protein of the present invention include, for example, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma or other respiratory problems. Other conditions, in which immune suppression is desired (including, for example, asthma and related respriatory conditions), may also be treatable using a protein of the present invention.

A protein of the present invention may also suppress chronic or acute inflammation, such as, for example, that associated with infection (such as septic shock or systemic inflammatory response syndrome (SIRS)), inflammatory bowel disease, Crohn's disease or resulting from over production of cytokines such as TNF or IL-1 (such as the effect demonstrated by IL-11).

The activity of a protein of the invention may, among other means, be measured by the following methods:

Suitable assays for thymocyte or splenocyte cytotoxicity include, without limitation, those described in: *Current Protocols in Immunology*, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al, J. Immunol. 128:1968–1974, 1982; Handa et al., J. Immunol. 135:1564–1572, 1985; Takai et al., J. Immunol. 137:3494–3500, 1986; Bowmanet al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In

*Current Protocols in Immunology.* J. E. e.a. Coligan eds. Vol 1 pp.3.8.1–3.8.16, John Wiley and Sons, Toronto. 1994.

Mixed lymphocyte reaction (MLR) assays (which will identify, among others, proteins that generate predominantly Thl and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by denritic cells that activate naive T-cells) include, without limitation, those described in: Guery et al., J. Immunol. 134:536–544, 1995; Inaba et al., Journal of Experimenal Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentarily to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e. in conjunction with bone marrow transplantation) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentation hematopoiesis) include, without limitation, those described in: Johansson et al. Cellular Biology 15:141–51, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In *Culture of Hematopoietic Cells.* R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In *Culture of Hematopoietic Cells.* R. L Freshney, et aL eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture ofHematopoietic Cells.* R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells.* R. I. Freshney, et al. eds. Vol pp. 163–179, Wiley-Liss, Inc., New York, N.Y. 1994; Long term culture initating cell assay, Sutherland, H. J. In *Culture of Hematopoietic Cells.* R. I. Freshney, et al. eds. Vol pp. 139–162, Wiley-Liss, Inc., New York, N.Y. 1994.

CTLA-8 proteins are useful in the treatment of various immune deficiencies and disorders (including SCID), e.g., in regulating (up or down) growth, proliferation and/or activity of T and/or B lymphocytes, as well as the cytolytic activity of NK cells. These immune deficiencies may be caused by viral (e.g., HIV) as well as bacterial infections, or may result from autoimmune disorders. More specifically, infectious diseases caused by viral, bacterial, fungal or other infection may be treatable using CTLA-8 proteins, including infections by HIV, hepatitis, influenza, CMV, herpes, mycobacterium, leishmaniasis, malaria and various fungal infections (such as candida). Of course, in this regard, the CTLA-8 proteins may also be useful where a boost to the immune system generally would be indicated, i.e., in the treatment of cancer or as an adjuvant to vaccines. Autoimmune disorders which may be treated using factors of the present invention include, for example, multiple sclerosis, systemic lupus erythematosus, rheumatoid arthritis, autoimmune pulmonary inflammation, Guillain-Barre syndrome, autoimmune thyroiditis, insulin dependent diabetes melitis and autoimmune inflammatory eye disease. The CTLA-8 proteins are also expected to be useful in the treatment of allergic reactions and conditions.

CTLA-8 proteins are also expected to have chemotactic activity A protein or peptide has "chemotactic activity," as used herein, if it can stimulate, directly or indirectly, the directed orientation or movement of cells, including myeloid and lymphoid cells. Preferably, the protein or peptide has the ability to directly stimulate directed movement of cells (particularly T-cells). Whether a particular protein or peptide has chemotactic activity for cells can be readily determined by employing such protein or peptide in any known assay for cell chemotaxis.

CTLA-8 proteins also inhibit growth and proliferation of vascular endothelial cells. As a result, human CTLA-8 proteins are effective in inhibiting angiogenesis (i.e., vascular formation). This activity will also be useful in the treatment of tumors and other conditions in which angiogenesis in involved. Inhibition of angiogenesis by human CTLA-8 proteins will also result in inhibition or prevention of the condition to which normal angiogenesis would contribute.

Isolated CTLA-8 proteins, purified from cells or recombinantly produced, may be used as a pharmaceutical composition when combined with a pharmaceutically acceptable carrier. Such a composition may contain, in addition to CTLA-8 protein and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-15,G-CSF, γ-IFN, stem cell factor, and erythropoietin. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with CTLA-8 protein, or to minimize side effects caused by the CTLA-8 protein. Conversely, CTLA-8 protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which CTLA-8 protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of CTLA-8 protein is administered to a mammal. CTLA-8 protein may be administered in accordance with the method of the invention either alone or in combination with other therapies such as treatments employing cytokines, lymphokines or other hematopoietic factors. When co-administered with one or more cytokines, lymphokines, other hematopoietic factors or vaccine components (such as antigens or other adjuvants), CTLA-8 protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering CTLA-8 protein in combination with cytokine(s), lymphokine(s), other hematopoietic factor(s), thrombolytic or anti-thrombotic factors.

Administration of CTLA-8 protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of CTLA-8 protein is administered orally, CTLA-8 protein will be in the form of a tablet, capsule, powder, solution or elixir. When administered in tablet form, the pharmaceutical composition of the invention may additionally contain a solid carrier such as a gelatin or an adjuvant The tablet, capsule, and powder contain from about 5 to 95% CTLA-8 protein, and preferably from about 25 to 90% CTLA-8 protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of CTLA-8 protein, and preferably from about 1 to 50% CTLA-8 protein.

When a therapeutically effective amount of CTLA-8 protein is administered by intravenous, cutaneous or subcutaneous injection, CTLA-8 protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to CTLA-8 protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of CTLA-8 protein in the pharmaceutical composition of the present invention will depend upon the nature and severity of the condition being treated, and on the nature of prior treatments which the patient has undergone.

Ultimately, the attending physician will decide the amount of CTLA-8 protein with which to treat each individual patient. Initially, the attending physician will administer low doses of CTLA-8 protein and observe the patient's response. Larger doses of CTLA-8 protein may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of CTLA-8 protein per kg body weight, preferably about 0.1 pg to about 10 mg of CTLA-8 protein per kg body weight, more preferably about 0.1 µg to about 100 µg of CTLA-8 protein per kg body weight, most preferably preferably about 0.1 µg to about 10 µg of CTLA-8 protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the CTLA-8 protein will be in the range of 12 to 24 hours of continuous intravenous administration. Ultimately the attending physician will decide on the appropriate duration of intravenous therapy using the pharmaceutical composition of the present invention.

CTLA-8 protein of the invention may also be used to immunize animals to obtain polyclonal and monoclonal antibodies which specifically react with the CTLA-8 protein and which may inhibit CTLA-8 binding to its receptor. Such antibodies are also useful for performing diagnostics assays for CTLA-8 in accordance with known methods. Such antibodies may be obtained using the entire CTLA-8 protein as an immunogen, or by using fragments of human CTLA-8 protein. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Neutralizing or non-neutralizing antibodies (preferably monoclonal antibodies) binding to human CTLA-8 protein may also be usefull therapeutics for certain tumors and also in the treatment of conditions described above. These neutralizing monoclonal antibodies are capable of blocking the ligand binding to the human CTLA-8 protein or mayh promote clearance of protein from the patient.

Because of their homology to human CTLA-8, rat CTLA-8 proteins, herpes CTLA-8 proteins and IL17 proteins (the "human CTLA-8" of Golstein et al., supra) will also possess CTLA-8 activity as described above. As a result, rat and herpes CTLA-8 proteins and IL-17 proteins, as well as active fragments and variants thereof, can be used in preparation of pharmaceutical compositions and in methods of treatment as described for human CTLA-8. Rat and herpes CTLA-8 proteins, and active fragments and variants thereof, can be produced as described above using the polynucleotides (or fragments or variants thereof) described in SEQ ID NO:3 and SEQ ID NO:5, respectively. Rat and herpes CTLA-8 may also be produced as described in Rouvier et al., J. Immunol. 1993, 150, 5445–5456. CTLA-8 proteins of other species can also be used as described herein. cDNAs encoding rat CTLA-8 and herpes CTLA-8 were deposited with the American Type Culture Collection on Jul. 6, 1995 and assigned accession numbers ATCC 69867 and ATCC 69866, respectively. IL-17 proteins may also be produced as described in Golstein et al., supra.

Because of its homology to IL-17, the human CTLA-8 (B18) proteins of the present invention may also share some activities with IL-17.

For the purposes of treatment or therapy, any of the proteins discussed or disclosed herein may be administered by in vivo expression of the protein in a mammalian subject. In such instances, a polynucleotide encoding the desired protein is administered to the subject in manner allowing expression in accordance with known methods, including without limitation the adenovirus methods disclosed herein.

EXAMPLE 1

Isolation of Human CTLA-8 cDNA

A partial clone for human CTLA-8 was isolated from a cDNA library made from RNA isolated from stimulated human peripheral blood mononuclear cells. This partial was identified as "B 18." B 18 is sometimes used herein to refer to the human CTLA-8 of the present invention. Homology searches identified this partial clone as being related to the herpes and rat CTLA-8 genes. DNA sequence of this partial clone was used to isolate the full-length clone.

In order to isolate a full-length cDNA for B 18, a directional, full-length cDNA library by standard means in the COS expression vector pMV2. The cDNA library was transformed into E. coli by electroporation. The bulk of the original transformed cDNA library was frozen in glycerol at –80° C. An aliquot was titered to measure the concentration of transformed E. coli. The E. coli were thawed, diluted to 76,000/0.1 ml in media containing ampicillin, and 0.1 ml was distributed into the wells of a microtiter dish in an 8×8 array. The microtiter dish was placed at 37° C. overnight to grow the E. coli.

To prepare DNA for PCR, 20 µl aliquots of culture from each well were withdrawn and pooled separately for each row and column of eight wells, giving 16 pools of 160 µl each. The E. coli were pelleted, resuspended in 160 µl of standard lysis buffer consisting of 10 mM TrisHCl pH8, 1 mM EDTA, 0.01% Triton X-100, and lysed by heating to 95° C. for 10 minutes.

To identify which of the wells contained E. coli transformed with B 18, PCR was performed first on the DNA preps corresponding to the eight columns. The PCR consisted of two sequential reactions with nested oligonucleotides using standard conditions. The oligonucleotides used for the PCR reaction were derived from the sequence of the partial B 18 clone. They were:

B185: CACAGGCATACACAGGAAGATACATTCA (SEQ ID NO:7)

B183: TCTTGCTGGATGGGAACGGAATTCA (SEQ ID NO:8)

B18N: ATACATTCACAGAAGAGCTTCCTGCACA (SEQ ID NO:9)

The PCR conditions were 2.5 mM MgCl$_2$ and 95° C.×2 min for one cycle, 95° C.×1 min plus 68° C.×1 mnin for 30 cycles, and 68° C.×10 for one cycle. Each reaction was 20 µl. The first reaction contained oligonucleotides B185 and B183 and 1 µl of the DNA preparations. The second reaction contained oligonucleotides B183 and B18N and 1 µl of the first reaction.

DNA preps that potentially contained a full-length B18 cDNA clone were identified by agarose gel electrophoresis on an aliquot of the second PCR reaction. A DNA band of the correct mobility was assumed to be derived from a B18 cDNA. Next the same sequence of PCR reactions and gel analysis was done on the DNA preps corresponding to the eight rows. The intersection of a row and a column identified well A2 as potentially containing B18, narrowing it down to the 76,000 E. coli originally seeded into that well.

To further purify the individual E. coli containing the putative full-length B18 cDNA clone, the concentration of E. coli in well A2 was measured by titering and plating dilutions of the well. Then 7600 E. coli were seeded into the wells of a second microtiter plate in an 8×8 array. The E. coli were grown overnight; wells were pooled, and DNA was prepared as described above. To identify which of these wells contained E. coli transformed with B18, sequential PCR reactions were performed essentially as described above. Agarose gel electrophoresis identified well B2 as potentially containing a B18 cDNA.

The E. coli containing this cDNA was further purified by seeding wells of a microtiter plate with 253 E. coli per well and proceeding as for the purification of the E. coli in well A2. Well C3 was identified as containing a putative full-length B18 cDNA clone. The exact E. coli was identified by plating the contents of the well onto bacterial culture media and then screening the E. coli colonies following established protocols. The probe for these hybridizations was a PCR fragment generated by doing a PCR reaction on the B18 clone using as primers the oligonucleotides described above (SEQ ID NO:7, SEQ ID NO:8, SEQ ID NO:9). When a single colony was identified, DNA was prepared and sequenced by standard methods. Comparison of this sequence to the sequence of the original partial clone confirmed identity and that the isolated cDNA was full-length.

The full-length clone was deposited with the American Type Culture Collection on Jul. 6, 1995 and assigned accession number ATCC 69868.

EXAMPLE 2

Expression of Human CTLA-8

The full-length B18 clone for human CTLA-8 was transfected into COS cells which were then labelled with $^{35}$S-methionine. An aliquot of conditioned medium from the transfected cell culture was reduced, denatured and electrophoresed on polyacrylamide gels. Autoradiographs of those gels are reproduced in FIG. 2. The band indicated by the arrow demonstrates expression of human CTLA-8.

EXAMPLE 3

Inhibition of Angiogenesis by Human CTLA-8

Figure 3:
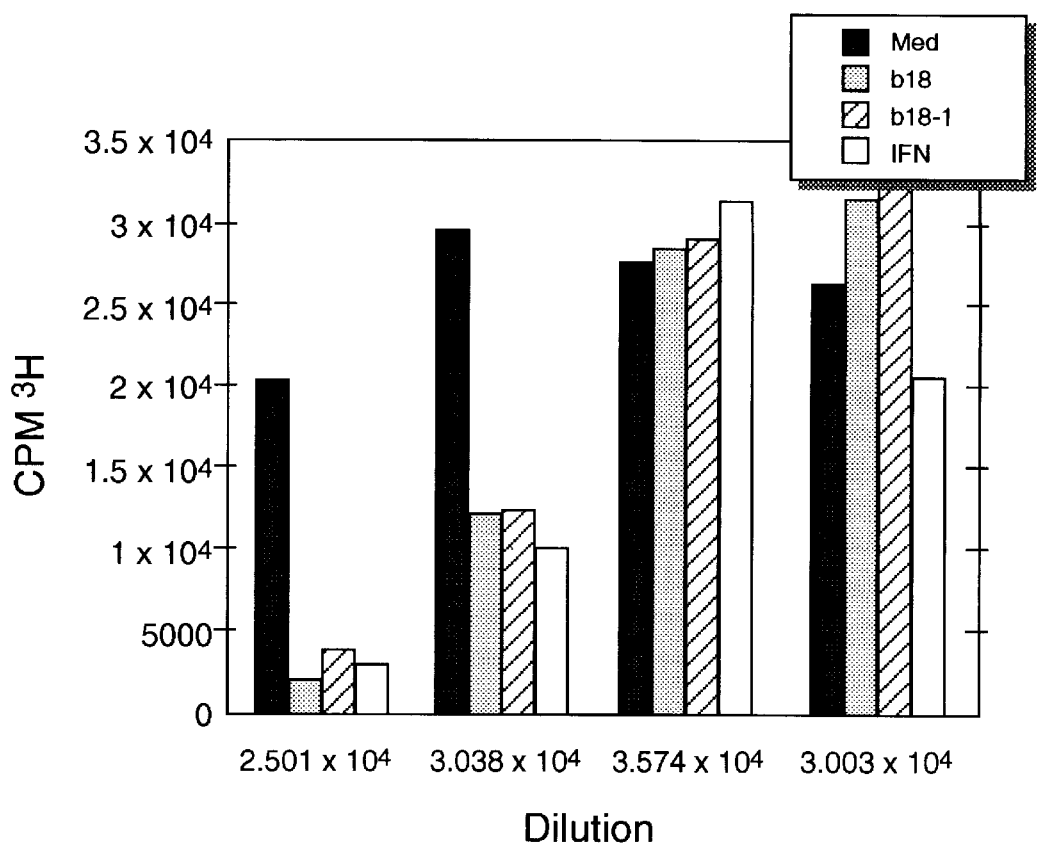
FIG. 3 presents data relating to the ability of human CTLA-8 to inhibit angiogenesis.
Figure 4A:
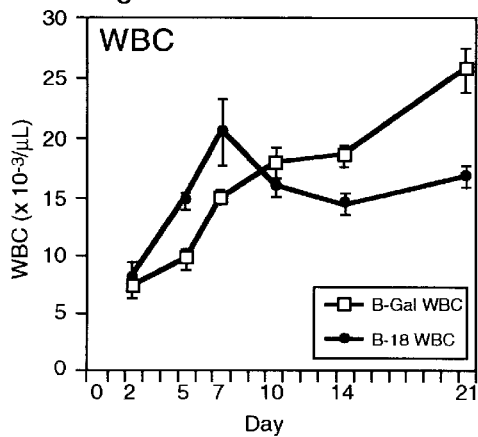
FIGS. 4 and 5 present data relating to the ability of human CTLA-8 to produce or induce hematopoietic activity.
Figure 4B:
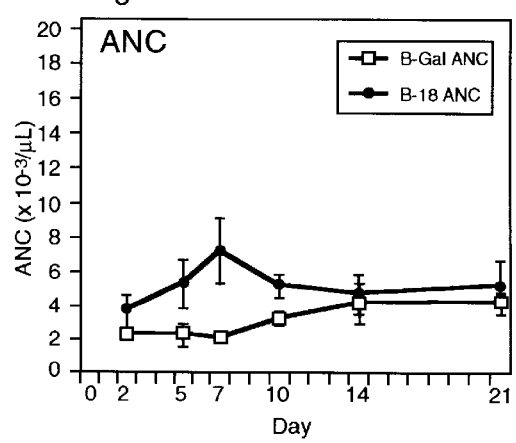
Figure 4C:
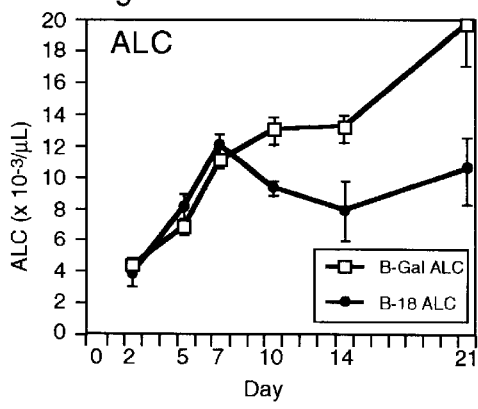
Figure 4D:
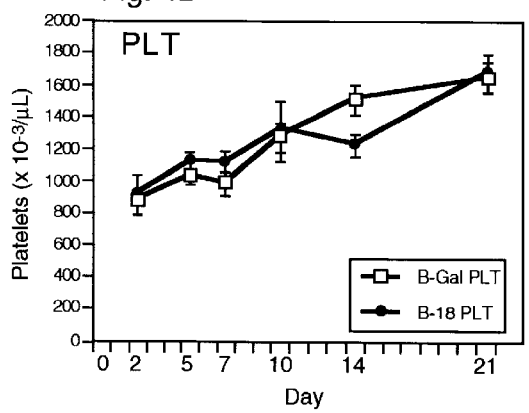

The ability of human CTLA-8 to inhibit angiogenesis was examined in an angiostatic activity assay (endothelial cell proliferation assay). The assay was done in a 96 well plate. Primary human umbilical cells (HUVECs) were seeded to $2\times10^3$ cells per well in EGM medium (Clonetics)/20% FCS and incubated at 37° C. for 24 hr. The cells were then starved in M199 medium (GIECO BRL) containing 10% charcoal treated serum (M199-CS) for 48 hr at 37° C. Conditioned media containing B18 (human CTLA-8) was obtained from transfected COS or stably expressing CHO cells and 1:10, 1:50, 1:250, and 1:1250 dilutions prepared in M199-CS medium containing 100 ng/ml FGF. The dilutions of B18 were added to the starved cells and incubated for 72 hr at 37° C. The cells were then radiolabeled by [$^3$H]-thymidine for 6 hr. Radiolabeled cells were washed with PBS and trypsinized for liquid scintilation counting. Results were plotted using Kaleidograph software. The results are shown in FIG. 3. In the figure, "Med" is the mock control, "B18" and "B18-1" were conditioned medium from two independent transfections of COS with DNA encoding human CTLA-8 (B18). IFNγ was used as a positive control angiostatic (i.e., angiogenesis inhibition) activity. These data demonstrate that human CTLA-8 (B18) inhibits angiogenesis.

EXAMPLE 4

Hematopoietic Activity of Human CTLA-8

The hematopoietic activity of human CTLA-8 (B118) expressed in vivo was examined by construction of a recombinant adenovirus vector.

The B18 cDNA in the expression plasmid Adori 2–12 B18 was driven by the cytomegalovirus(CMV) immediate early promoter and enhancer.

The Adori 2–12 vector was created by addition of an SV40 origin and enhancer to a known adenovirus vector (Barr et al., Gene Therapy 1:51 (1994); Davidson et al., Nature Genetics 3:219 (1993)). The HindIII/BamHI fragment encoding the SV40 origin and enhancer was isolated from the pMT2 mammalian expression vector, blunted with Klenow and cloned into the NatI site (blunted with Klenow) of the Ad5 expression vector.

The vector was derived by digesting pNOT-B18 cDNA with Sal, filling in the 5' overhang with Klenow to generate a blunt end and digesting with EcoRI to isolate the B18 cDNA. The blunted- EcoRI B18 fragment was inserted into the restriction sites EcoRV-EcoRI of the adenovirus vector Adori 2–12. The CMV-B18 expression cassette was located downstream of the SV40 origin and enhancer, and 0–1 map units of the left hand end of the adenovirus type 5(Ad5). The SV40 splice donor and acceptor were located between the CMV promoter and B18 cDNA. Following the insert was SV40 poly A site, 9-16 map units of Ad5 and the puc 19 origin.

A recombinant adenovirus was generated by homologous recombination in 293 cells. AscI linearized Adori 2-12 B18 and ClaI digested AdCMVlacZ were introduced into the 293 cells using lipofectamine. Recombinant adenovirus virus was isolated and amplified on 293 cells. The virus was released from infected 293 cells by three cycles of freeze-thawing. The virus was further purified by two cesium chloride centrifugation gradients and dialyzed against PBS 4° C. Following dialysis of the virus glycerol was added to a concentration of 10% and the virus was stored at –70° C. until use. The virus was characterized by expression of the transgene, plaque forming units on 293 cells, particles/ml and Southern analysis of the virus.

A single dose of $5\times10^{10}$ particles of recombinant adenovirus encoding B18 was injected into the tail vein of male C57/b16 mice, age 7–8 weeks. Control mice received an adenovirus encoding B-galactosidase. Four mice from each experimental group were killed on day 7 and 14. Blood was collected and automated hematologic analysis was performed using a Baker 9000. Differential counts were performed on blood smears. Tissue was harvested, fixed in formalin, and stained with hematoxylin and eosin for histopathology. In the first set of experiments, serum and tissues were analyzed 7 and 14 days post injection. A slight increase in peripheral platelet counts were observed. The animals that received B18 exhibited a slight increase in spleen size. Macroscopic analysis of the spleen showed an increase in splenic extramedullary hematopoiesis on day 7 compared to the control. These results showed a hematopoietic growth activity associated with B18.

In a second set of experiments 5×10$^{10}$ particles of recombinant adenovirus encoding B18 were injected into the tail vein of male C57/b16 mice, age 17–18 weeks. Control mice received an adenovirus encoding B-galactosidase. Blood samples were collected via retro-orbital sinus on days 2, 5, 7, 10, 14, and 21. The hematologic analyses were performed on the Baker 9000 automated cell counter with murine-specific settings. Analyses included WBC, RBC, HCT and PLT counts. Blood smears were prepared and stained with Wright-Geimsa for WBC differentials based on a 100 cellcount. Reticulocytes and reticulated platelets were quantitated using flow cytometry. Four mice from each group were killed on days 7, 14, and 21. In addition to peripheral blood analysis, serum was collected via cardiac puncture for quantitation of systemic 1–6 using a commercial kit (Endogen). Spleen and liver were collected for histopathology, spleen and bone marrow hematopoietic progenitors were quantitated, and bone marrow smears were prepared and stained with Wright-Geimsa for cell counts.

Administration of adenovirus encoding B18 resulted in a marked increase in peripheral blood neutrophils and WBC (FIG. 4). Maximum increases in neutrophils were observed at day 5 and day 7. The control mice showed little difference at day 5 and day 7. Peripheral blood neutrophils were similar in the control mice and mice that received B18 at day 21. In both the B18 and control groups an increase in white blood cells was also observed. The mice that received B18 had a greater increase in WBC between day 2 and day 7. By Day 21 a more pronounced increase was observed in the B-gal group. No other changes in cellular chemistries were observed (Table I).

Bone marrow cellularity was calculated from pooled femurs in each group (Table III). No significant differences were observed in either group. No significant changes were observed in bone marrow hematopoietic progenitors from day 7, 14, and 21. The CFU-GM, BFU-E and CFU-MEG in the B18 mice were similar to the B-gal control (Table II).

Administration of the adenovirus encoding B18 resulted in an increase in CFU-GM (myeloid) and BFU-E (erythroid) progenitors in the spleen compared to animals that received the B-gal virus on day 7. The increase in progenitors in the B18 mice was 11-fold in CFU-GM and a 52-fold in BFU-E (Table II). There was a 2-fold increase in CFU-MEG at day 7 for the B18 mice. By day 21 no significant differences were observed in splenic CFU-MEG or BFU-E between the groups (Table II). A 3-fold decrease in CFU-GM was observed in mice that received adenovirus encoding B18. A slight increase in spleen size at day 7 was observed in the B18 group. This is consistent with an increase in splenic cellularity. By day 14 and day 21 spleen weights were similar to the control group (Table III). Macroscopic analysis of the spleen showed an increase in splenic extramedullary hematopoiesis of the B18 mice on day 7 compared to the control.

The bone marrow myeloid: erythroid ratios (Table IV) suggest a granulocytic hyperplasia with a possible erythroid hypoplasia in mice that received adenovirus B18 on day 7. By day 21 the ratio in the B-gal group was higher. No changes were observed in the IL6 serum levels.

These results show a hematopoietic activity associated with the administration of adenovirus encoding B18 (human CTLA-8). Increases in neutrophils and white blood cells were observed at day 7 in animals that received B18 adenovirus. The data showed that B18 resulted in increase in splenic CFU-GM and BFU-E 7 days post administration compared to the control animals. Splenic extramedullary hematopoiesis on day 7 support that B18 exhibits a hematopoietic growth activity. These data suggest that B18 may moblize early hematopoietic precursors.

TABLE I

Peripheral hematology for day 2, 5, 7, 10, 14, and 21.

Study A54-4B . . . B18 (Platelets) Day 2 . . . 4-25-96.

| Group A | WBC ×10$^3$/uL | Neuts % | ANC ×10$^3$/uL | Lymphs % | ALC ×10$^3$/uL | Eos % | Monos % | RBC ×10$^6$/uL | Retics % | Abs Relics ×10$^6$/uL | HCT % | PLT ×10$^3$/uL | RPlt % | Abs RPlt ×10$^3$/uL |
|---|---|---|---|---|---|---|---|---|---|---|---|---|---|---|
| B-Gal #1 | 5.4 | 46 | 2.16 | 54 | 2.62 | 0 | 6 | 10.66 | 3.65 | 0.46 | 48.0 | 836 | 11.94 | 99.82 |
| B-Gal #2 | 7.4 | 25 | 1.85 | 65 | 4.81 | 3 | 7 | 12.34 | 2.04 | 0.25 | 56.6 | 900 | 10.10 | 90.90 |
| B-Gal #3 | 6.6 | 46 | 2.72 | 52 | 3.54 | 2 | 6 | 11.26 | 3.26 | 0.37 | 51.6 | 894 | 9.77 | 87.34 |
| B-Gal #4 | 6.6 | 23 | 2.02 | 64 | 5.63 | 1 | 12 | 12.00 | 2.55 | 0.31 | 54.8 | 840 | 10.63 | 89.29 |
| AVG | 7.1 | 32.0 | 2.19 | 58.8 | 4.22 | 1.5 | 7.8 | 11.62 | 2.88 | 0.33 | 52.8 | 868 | 10.61 | 91.84 |
| SEM | 0.7 | 4.6 | 0.19 | 3.4 | 0.61 | 6.6 | 1.4 | 0.33 | 0.36 | 0.03 | 1.9 | 17 | 0.48 | 2.76 |
| B18 #1 | 11.4 | 59 | 6.73 | 31 | 3.53 | 1 | 9 | 11.16 | 4.88 | 0.54 | 52.4 | 1242 | 14.92 | 185.31 |
| B18 #2 | 9.2 | 30 | 2.76 | 62 | 5.70 | 3 | 5 | 10.14 | 3.97 | 0.40 | 48.0 | 632 | 10.90 | 68.89 |
| B18 #3 | 5.0 | 51 | 2.55 | 40 | 2.00 | 0 | 9 | 11.16 | 3.23 | 0.36 | 51.2 | 832 | 11.18 | 93.02 |
| B18 #4 | 6.4 | 41 | 2.62 | 55 | 3.52 | 0 | 4 | 16.66 | 3.09 | 0.33 | 49.2 | 904 | 17.31 | 156.48 |
| AVG | 6.0 | 45.3 | 3.67 | 47.0 | 3.69 | 1.0 | 6.8 | 10.62 | 3.79 | 0.41 | 50.2 | 903 | 13.58 | 125.92 |
| SEM | 1.4 | 6.3 | 1.02 | 7.0 | 0.76 | 0.7 | 1.3 | 0.24 | 0.41 | 0.05 | 1.0 | 127 | 1.55 | 27.07 |

Study A54-4B . . . B18 (Platelets) Day 5 . . . 4-28-96.

| Group B | WBC ×10$^3$/uL | Neuts % | ANC ×10$^3$/uL | Lymphs % | ALC ×10$^3$/uL | Eos % | Monos % | RBC ×10$^6$/uL | Retics % | Abs Relics ×10$^6$/uL | HCT % | PLT ×10$^3$/uL | RPlt % | Abs RPlt ×10$^3$/uL |
|---|---|---|---|---|---|---|---|---|---|---|---|---|---|---|
| B-Gal #1 | 7.6 | 14 | 1.06 | 78 | 5.93 | 3 | 5 | 11.26 | 5.25 | 0.59 | 52.4 | 1082 | 15.51 | 167.82 |
| B-Gal #2 | 10.6 | 20 | 2.12 | 78 | 8.27 | 1 | 1 | 10.72 | 4.71 | 0.50 | 49.4 | 994 | 17.37 | 172.66 |
| B-Gal #3 | 8.8 | 18 | 1.51 | 69 | 6.07 | 2 | 11 | 11.12 | 3.40 | 0.38 | 51.2 | 916 | 9.55 | 87.48 |
| B-Gal #4 | 10.8 | 38 | 4.10 | 58 | 6.26 | 0 | 4 | 10.22 | 6.21 | 0.63 | 47.0 | 1092 | 13.93 | 152.12 |
| AVG | 9.5 | 22.5 | 2.20 | 70.8 | 6.63 | 1.5 | 5.3 | 10.83 | 4.89 | 0.53 | 50.0 | 1021 | 14.09 | 145.02 |

TABLE I-continued

Peripheral hematology for day 2, 5, 7, 10, 14, and 21.

| | | | | | | | | | | | | | | |
|---|---|---|---|---|---|---|---|---|---|---|---|---|---|---|
| SEM | 0.8 | 5.3 | 0.67 | 4.8 | 0.55 | 0.6 | 2.1 | 0.23 | 0.59 | 0.06 | 1.2 | 41 | 1.67 | 19.67 |
| B18 #1 | 14.8 | 18 | 2.66 | 71 | 10.51 | 1 | 10 | 12.66 | 2.31 | 0.29 | 57.0 | 1204 | 7.57 | 91.14 |
| B18 #2 | 14.2 | 37 | 5.25 | 53 | 7.53 | 2 | 8 | 9.80 | 3.32 | 0.33 | 44.6 | 888 | 14.33 | 127.25 |
| B18 #3 | 12.8 | 30 | 3.84 | 59 | 7.55 | 1 | 10 | 12.12 | 4.12 | 0.50 | 55.6 | 1134 | 10.15 | 115.10 |
| B18 #4 | 16.0 | 58 | 9.28 | 37 | 5.92 | 0 | 5 | 11.04 | 3.93 | 0.43 | 50.8 | 1166 | 15.75 | 183.65 |
| AVG | 14.5 | 35.8 | 5.26 | 550 | 7.88 | 1.0 | 8.3 | 11.41 | 3.42 | 0.39 | 52.0 | 1098 | 11.95 | 129.28 |
| SEM | 0.7 | 8.4 | 1.44 | 7.1 | 0.96 | 0.4 | 1.2 | 0.63 | 0.41 | 0.05 | 2.8 | 71 | 1.88 | 19.61 |

Study A54-4B ... B18 (Platelets) Day 7 ... 4-40-96.

| Group C | WBC ×10^3/uL | Neuts % | ANC ×10^3/uL | Lymphs % | ALC ×10^3/uL | Eos % | Monos % | RBC ×10^6/uL | Retics % | Abs Relics ×10^6/uL | HCT % | PLT ×10^3/uL | RPlt % | Abs_RPlt ×10^3/uL |
|---|---|---|---|---|---|---|---|---|---|---|---|---|---|---|
| B-Gal #1 | 15.2 | 14 | 2.13 | 69 | 10.49 | 1 | 16 | 11.04 | 3.54 | 0.39 | 50.8 | 862 | 12.46 | 107.41 |
| B-Gal #2 | 14.0 | 12 | 16.8 | 81 | 11.34 | 0 | 7 | 11.38 | 5.05 | 0.57 | 52.6 | 1104 | 14.91 | 164.81 |
| B-Gal #3 | 14.8 | 14 | 2.07 | 73 | 10.80 | 1 | 12 | 10.92 | 5.42 | 0.59 | 49.6 | 952 | 11.49 | 109.38 |
| AVG | 14.7 | 13.3 | 1.96 | 74.3 | 10.88 | 0.7 | 11.7 | 11.11 | 4.67 | 0.52 | 51.0 | 973 | 12.95 | 127.13 |
| SEM | 0.4 | 0.7 | 0.14 | 3.5 | 0.25 | 0.3 | 2.6 | 0.14 | 0.58 | 0.06 | 0.9 | 71 | 1.02 | 18.75 |
| B18 #1 | 19.4 | 33 | 6.40 | 62 | 12.03 | 0 | 5 | 10.14 | 2.93 | 0.30 | 45.2 | 864 | 12.80 | 110.59 |
| B18 #2 | 25.4 | 39 | 9.91 | 53 | 13.46 | 0 | 8 | 9.48 | 6.05 | 0.57 | 43.6 | 1288 | 12.49 | 160.87 |
| B18 #3 | 23.6 | 44 | 10.38 | 50 | 11.80 | 0 | 6 | 9.74 | 5.17 | 0.50 | 44.4 | 1076 | 15.41 | 165.81 |
| B18 #4 | 12.8 | 15 | 1.92 | 75 | 9.60 | 0 | 10 | 9.54 | 6.26 | 0.60 | 43.4 | 1136 | 15.88 | 180.40 |
| AVG | 20.3 | 32.8 | 7.15 | 60.0 | 11.72 | 0.0 | 7.3 | 9.72 | 5.10 | 0.49 | 44.2 | 1091 | 14.15 | 154.42 |
| SEM | 2.8 | 6.3 | 1.96 | 5.6 | 0.80 | 0.0 | 1.1 | 0.15 | 0.76 | 0.07 | 0.4 | 88 | 0.87 | 15.19 |

Study A54-4B ... B18 (Platelets) Day 10 ... 5-3-96.

| Group A | WBC ×10^3/uL | Neuts % | ANC ×10^3/uL | Lymphs % | ALC ×10^3/uL | Eos % | Monos % | RBC ×10^6/uL | Retics % | Abs Relics ×10^6/uL | HCT % | PLT ×10^3/uL | RPlt % | Abs_RPlt ×10^3/uL |
|---|---|---|---|---|---|---|---|---|---|---|---|---|---|---|
| B-Gal #1 | 18.8 | 17 | 3.16 | 69 | 12.83 | 3 | 11 | 10.22 | 12.41 | 1.27 | 46.8 | 1460 | 16.20 | 236.52 |
| B-Gal #2 | 13.2 | 16 | 2.11 | 79 | 10.43 | 1 | 4 | 10.48 | 6.0 | 0.63 | 46.6 | 1128 | 14.48 | 163.33 |
| B-Gal #3 | 19.6 | 16 | 3.14 | 74 | 14.50 | 0 | 10 | 10.72 | 6.24 | 0.67 | 49.4 | 1338 | 16.58 | 221.84 |
| B-Gal #4 | 18.6 | 21 | 3.91 | 72 | 13.39 | 3 | 4 | 10.44 | 7.59 | 0.79 | 48.4 | 1068 | 14.35 | 153.26 |
| AVG | 17.5 | 17.5 | 3.08 | 73.5 | 12.79 | 1.8 | 7.3 | 10.47 | 8.06 | 0.84 | 46.4 | 1249 | 15.40 | 193.74 |
| SEM | 1.5 | 1.2 | 0.37 | 2.1 | 0.86 | 0.8 | 1.9 | 0.18 | 1.49 | 0.15 | 0.6 | 91 | 0.58 | 20.76 |
| B18 #1 | 14.2 | 33 | 4.69 | 56 | 7.95 | 5 | 6 | 8.70 | 11.97 | 1.04 | 39.2 | 1760 | 14.49 | 255.02 |
| B18 #2 | 17.6 | 35 | 6.16 | 57 | 10.03 | 1 | 7 | 9.04 | 9.48 | 0.86 | 42.0 | 1104 | 16.88 | 208.44 |
| B18 #3 | 16.2 | 39 | 6.32 | 57 | 9.23 | 1 | 3 | 4.74 | 16.77 | 0.79 | 22.4 | 894 | 29.19 | 260.96 |
| B18 #4 | 14.2 | 25 | 3.55 | 66 | 9.37 | 1 | 8 | 9.30 | 9.93 | 0.92 | 42.0 | 1416 | 16.81 | 238.03 |
| AVG | 15.6 | 33.0 | 5.18 | 59.0 | 9.15 | 2.0 | 6.0 | 7.95 | 12.04 | 0.90 | 36.4 | 1294 | 19.84 | 240.61 |
| SEM | 0.8 | 2.9 | 0.66 | 2.3 | 0.43 | 1.0 | 1.1 | 1.08 | 1.67 | 0.05 | 4.7 | 189 | 3.24 | 11.77 |

Study A54-4B ... B18 (Platelets) Day 14 ... 5-7-96.

| Group B | WBC ×10^3/uL | Neuts % | ANC ×10^3/uL | Lymphs % | ALC ×10^3/uL | Eos % | Monos % | RBC ×10^6/uL | Retics % | Abs Relics ×10^6/uL | HCT % | PLT ×10^3/uL | RPlt % | Abs_RPlt ×10^3/uL |
|---|---|---|---|---|---|---|---|---|---|---|---|---|---|---|
| B-Gal #1 | 17.8 | 18 | 3.20 | 74 | 13.17 | 0 | 8 | 10.86 | 5.97 | 0.65 | 50.8 | 1360 | 11.03 | 150.01 |
| B-Gal #2 | 20.4 | 26 | 5.30 | 66 | 13.46 | 1 | 7 | 10.92 | 7.07 | 0.77 | 50.8 | 1616 | 8.18 | 132.19 |
| B-Gal #3 | 16.0 | 7 | 1.12 | 90 | 14.40 | 1 | 3 | 11.36 | 6.41 | 0.73 | 52.8 | 1298 | 7.36 | 95.53 |
| B-Gal #4 | 18.0 | 36 | 6.48 | 57 | 10.26 | 1 | 6 | 9.30 | 7.62 | 0.71 | 43.0 | 1672 | 10.05 | 168.04 |
| AVG | 18.1 | 21.8 | 4.03 | 71.8 | 12.82 | 0.8 | 6.0 | 10.61 | 6.77 | 0.71 | 49.4 | 1487 | 9.16 | 136.44 |
| SEM | 0.9 | 6.1 | 1.18 | 7.0 | 0.89 | 0.3 | 1.1 | 0.45 | 0.36 | 0.03 | 2.2 | 93 | 0.84 | 15.48 |
| B18 #1 | 15.4 | 9 | 1.39 | 81 | 12.47 | 1 | 9 | 10.62 | 5.74 | 0.61 | 48.2 | 1262 | 9.51 | 120.02 |
| B18 #2 | 15.4 | 31 | 4.77 | 58 | 8.93 | 2 | 9 | 9.76 | 10.33 | 1.01 | 44.6 | 1093 | 14.29 | 156.05 |
| B18 #3 | 13.4 | 42 | 5.63 | 39 | 5.23 | 0 | 19 | 10.34 | 4.99 | 0.52 | 46.6 | 1376 | 15.79 | 217.27 |
| B18 #4 | 11.6 | 57 | 6.61 | 34 | 3.94 | 2 | 7 | 9.38 | 5.57 | 0.52 | 43.0 | 1092 | 16.66 | 181.93 |
| AVG | 14.0 | 34.8 | 4.60 | 53.0 | 7.64 | 1.3 | 11.0 | 10.03 | 6.66 | 0.66 | 45.6 | 1206 | 14.06 | 168.82 |
| SEM | 0.9 | 10.1 | 1.14 | 10.7 | 1.93 | 0.5 | 2.7 | 0.28 | 1.23 | 0.12 | 1.1 | 70 | 1.59 | 20.54 |

Study A54-4B ... B18 (Platelets) Day 21 ... 5-14-96.

| Group B | WBC ×10^3/uL | Neuts % | ANC ×10^3/uL | Lymphs % | ALC ×10^3/uL | Eos % | Monos % | RBC ×10^6/uL | Retics % | Abs Relics ×10^6/uL | HCT % | PLT ×10^3/uL | RPlt % | Abs_RPlt ×10^3/uL |
|---|---|---|---|---|---|---|---|---|---|---|---|---|---|---|
| B-Gal #1 | 25.4 | 23 | 5.84 | 67 | 17.02 | 0 | 10 | 9.22 | 8.15 | 0.75 | 42.8 | 1776 | 9.61 | 170.67 |
| B-Gal #2 | 19.6 | 19 | 3.72 | 69 | 13.52 | 0 | 12 | 9.50 | 9.95 | 0.95 | 44.4 | 1652 | 9.44 | 156.89 |
| B-Gal #3 | 27.6 | 11 | 3.04 | 82 | 22.63 | 3 | 4 | 9.74 | 8.84 | 0.66 | 45.8 | 1684 | 11.45 | 192.82 |
| B-Gal #4 | 28.0 | 13 | 3.64 | 83 | 23.24 | 0 | 4 | 9.04 | 7.54 | 0.68 | 41.6 | 1346 | 10.48 | 141.06 |
| AVG | 25.2 | 16.4 | 4.06 | 75.3 | 19.10 | 0.8 | 7.5 | 9.36 | 8.62 | 0.81 | 43.7 | 1617 | 10.25 | 165.36 |
| SEM | 1.9 | 2.8 | 0.61 | 4.2 | 2.33 | 0.6 | 2.1 | 0.15 | 0.52 | 0.06 | 0.9 | 94 | 0.46 | 10.97 |
| B18 #1 | 18.6 | 9 | 1.67 | 83 | 15.44 | 1 | 7 | 9.84 | 7.40 | 0.73 | 43.8 | 1642 | 8.37 | 137.44 |

TABLE I-continued

Peripheral hematology for day 2, 5, 7, 10, 14, and 21.

| | | | | | | | | | | | | | | |
|---|---|---|---|---|---|---|---|---|---|---|---|---|---|---|
| B18 #2 | 16.2 | 48 | 7.78 | 45 | 7.29 | 1 | 6 | 11.10 | 7.97 | 0.88 | 51.4 | 1970 | 10.79 | 212.37 |
| B18 #3 | 14.8 | 53 | 7.84 | 42 | 6.22 | 0 | 5 | 7.52 | 20.26 | 1.52 | 38.0 | 1568 | 10.50 | 164.64 |
| B18 #4 | 15.2 | 18 | 2.74 | 74 | 11.25 | 2 | 6 | 9.64 | 7.02 | 0.68 | 43.0 | 1422 | 7.60 | 108.07 |
| AVG | 16.2 | 32.0 | 5.01 | 61.0 | 10.05 | 1.0 | 6.0 | 9.53 | 10.66 | 0.95 | 44.1 | 1651 | 9.31 | 155.63 |
| SEM | 0.9 | 10.9 | 1.63 | 10.3 | 2.10 | 0.4 | 0.4 | 0.74 | 3.21 | 0.20 | 2.6 | 116 | 0.78 | 22.16 |

TABLE II

Bone marrow and Splenic Hematopoietic Progenitors

| Bone Marrow* | CFU-MEG | | CFU-GM | | BFU-E | |
|---|---|---|---|---|---|---|
| | B-Gal | B18 | B-Gal | B18 | B-Gal | B18 |
| Day 7 | 16.0 ± 3.5 | 15.7 ± 3.1 | 307 ± 117 | 241 ± 78 | 51 ± 19 | 25 ± 11 |
| Day 14 | 10.7 ± 2.3 | 15.3 ± 1.2 | 233 ± 15 | 373 ± 35 | 30 ± 10 | 60 ± 30 |
| Day 21 | 5.7 ± 0.6 | 6.7 ± 3.1 | 170 ± 17 | 160 ± 27 | 40 ± 10 | 27 ± 6 |
| Spleen** | | | | | | |
| Day 7 | 9.3 ± 1.6 | 19.5 ± 1.5 | 27 ± 3 | 298 ± 6 | 1.3 ± 1.2 | 68 ± 10 |
| Day 14 | 9.7 ± 0.6 | 12.7 ± 0.6 | 267 ± 32 | 197 ± 21 | 33 ± 6 | 10 ± 10 |
| Day 21 | 17.0 ± 1.0 | 19.3 ± 2.5 | 187 ± 6 | 73 ± 15 | 23 ± 6 | 23 ± 6 |

Hematopoietic precursors were determined form pooled spleen and bone marrow samples from four animals in each group. For quantitation of CFU-GM and BFU-E, either $1 \times 10^4$ bone marrow cells or $1 \times 10^5$ spleen cells were added to complete alpha methylcelluose medium (0.9% methylcellulose in alpha medium, 30% fetal bovine serum, 1% bovine serum albumin, 10-4M 2-mercaptoethanol, 2 mM L-glutamine, 2% murine spleen cell conditioned medium, and 3 U/mL erythropoietin) and aliquoted into 35 mm tissue culture dishes in a final volume of 1.0 mL. Cultures were incubated for 7 days at 37° C., and 5% $CO_2$. Microscopic colonies were defined as clusters of 50 or more cells. For quantitaion of CFU-MEG, either $1 \times 10^5$ bone marrow cells or $1 \times 10^6$ spleen cells were added to complete alpha methylcellulose medium and incubated as described above. Megakaryocyte colonies were defined as a group of 3 or more cells.

*Bone marrow progenitors are represented as mean±sd number of colonies per $10^5$ cells.
**Spleen progenitors are represented as mean±sd number of colonies per $10^6$ cells.

TABLE III

Spleen Weights and Femur Cellularity

| Spleen Wt. (Mg) | B-Gal | B18 | Femur Cellularity (× $10^6$) | B-Gal | B18 |
|---|---|---|---|---|---|
| Day 7 | 187 ± 19 | 224 ± 29 | Day 7 | 28 | 23 |
| Day 14 | 175 ± 13 | 170 ± 10 | Day 14 | 28 | 27 |
| Day 21 | 174 ± 21 | 151 ± 27 | Day 21 | 28 | 26 |

Spleen weights were determined at time of sacrifice are represented as means±sd from four animals.

TABLE IV

Bone Marrow Myeloid:Erythoid Ratios

| Group | Mouse # | Day 7 | Day 14 | Day 21 |
|---|---|---|---|---|
| B-gal | 1 | 1.43 | 2.12 | 5.78 |
| | 2 | 0.91 | 2.46 | 5.83 |
| | 3 | 1.62 | 1.03 | 3.66 |
| | 4 | | 5.44 | 4.82 |
| AVG | | 1.32 | 2.76 | 5.02 |
| SD | | 0.37 | 0.37 | 1.89 |
| B-gal | 1 | 5.59 | 2.01 | 2.02 |
| | 2 | 6.51 | 1.25 | 2.13 |
| | 3 | 5.49 | 1.58 | 1.81 |
| | 4 | 0.50 | 2.51 | 2.92 |
| AVG | | 4.52 | 1.86 | 2.22 |
| SD | | 1.29 | 2.72 | 0.56 |

All entries represent the number of myeloid cells per 1 erythroid cell. Normal mouse ratios are approximately 1:1 to 2:1.

EXAMPLE 5

Additional Experiments Relating to Hematopoietic Activity of Human CTLA-8

B18 (human CTLA-8) was tested for the ability to induce production of factors having hematopoietic activity in a factor-dependent cell proliferation assay using the human erythroleukemic cell line, TF-1 (Kitamura et al., J. Cell Physiol. 140:323 (1989)). The cells were initially grown in the presence of rhGMCSF (100 U/ml). The cells were fed three days prior to setting up the assay. The assay conditions were as follows:

| | |
|---|---|
| cells/well | 5000/200 µl |
| incubation time | 3 days |
| pulse time | 4 hours |
| amount of tritiated thymidine | 0.5 µCi/well |
| counting time | 1 minute |
| replicates | 2 |

Figure 5:
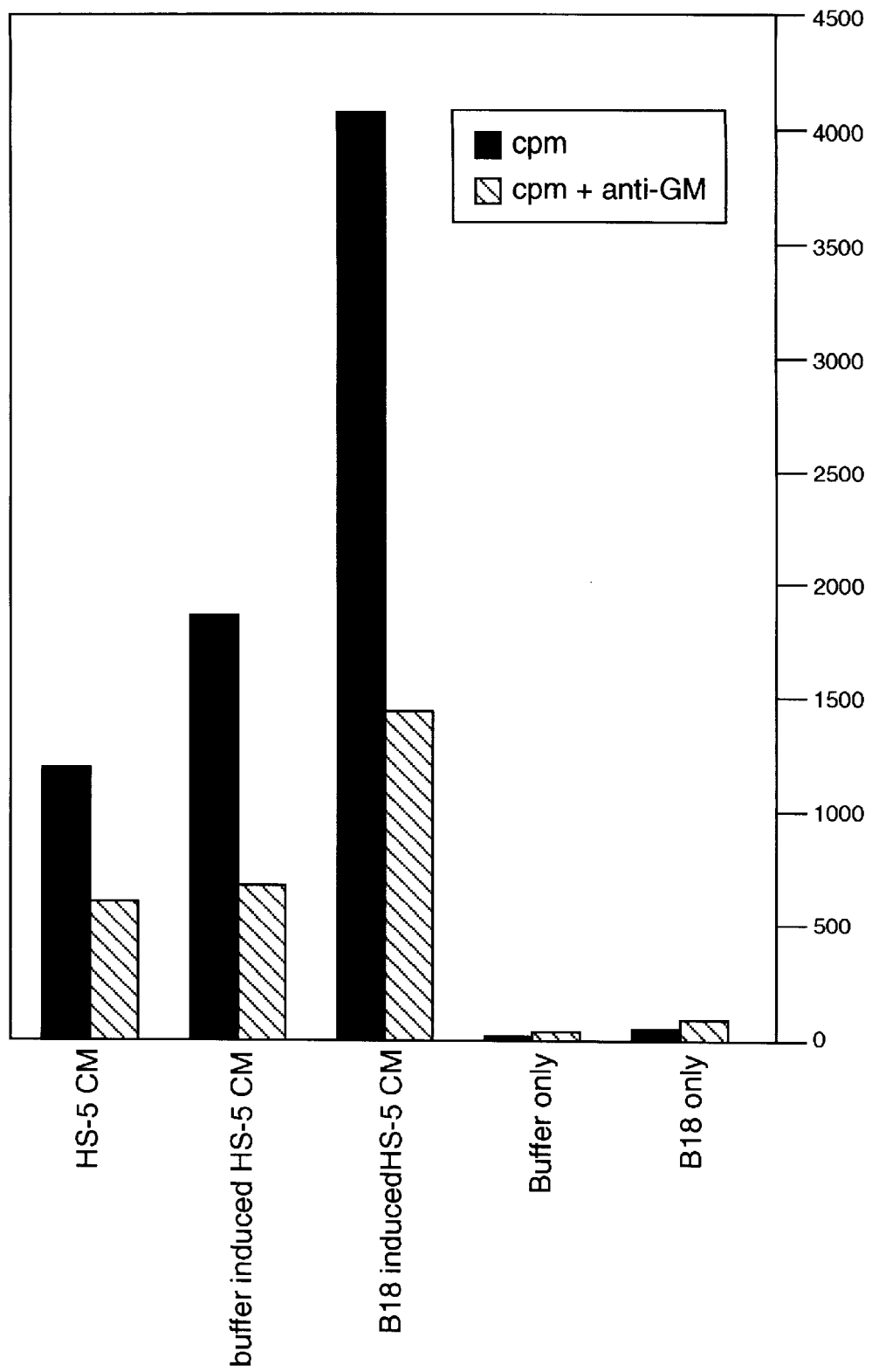

B18 alone, conditioned medium (CM) from B18 induced HS-5 cells were assayed. Buffer alone, CM from HS-5 cells induced with buffer and CM from uninduced HS-5 cells were assayed as controls. Results are shown in FIG. 5. B18 (human CTLA-8) demonstrated an abilit to induce production of factors which induced TF-1 proliferation. This activity was substantially eliminated by the addition of anti-GMCSF antibodies. These data demonstrate that human CTLA-8 (B18) is able to induce hematopoiesis. Particularly, without being bound by any theory, it appears that human CTLA-8 (B18) induces production of GM-CSF and/or IL-3.

EXAMPLE 6

Ability of Human CTLA-8 to Induce Production of IL-6 and IL-8

Figure 6:
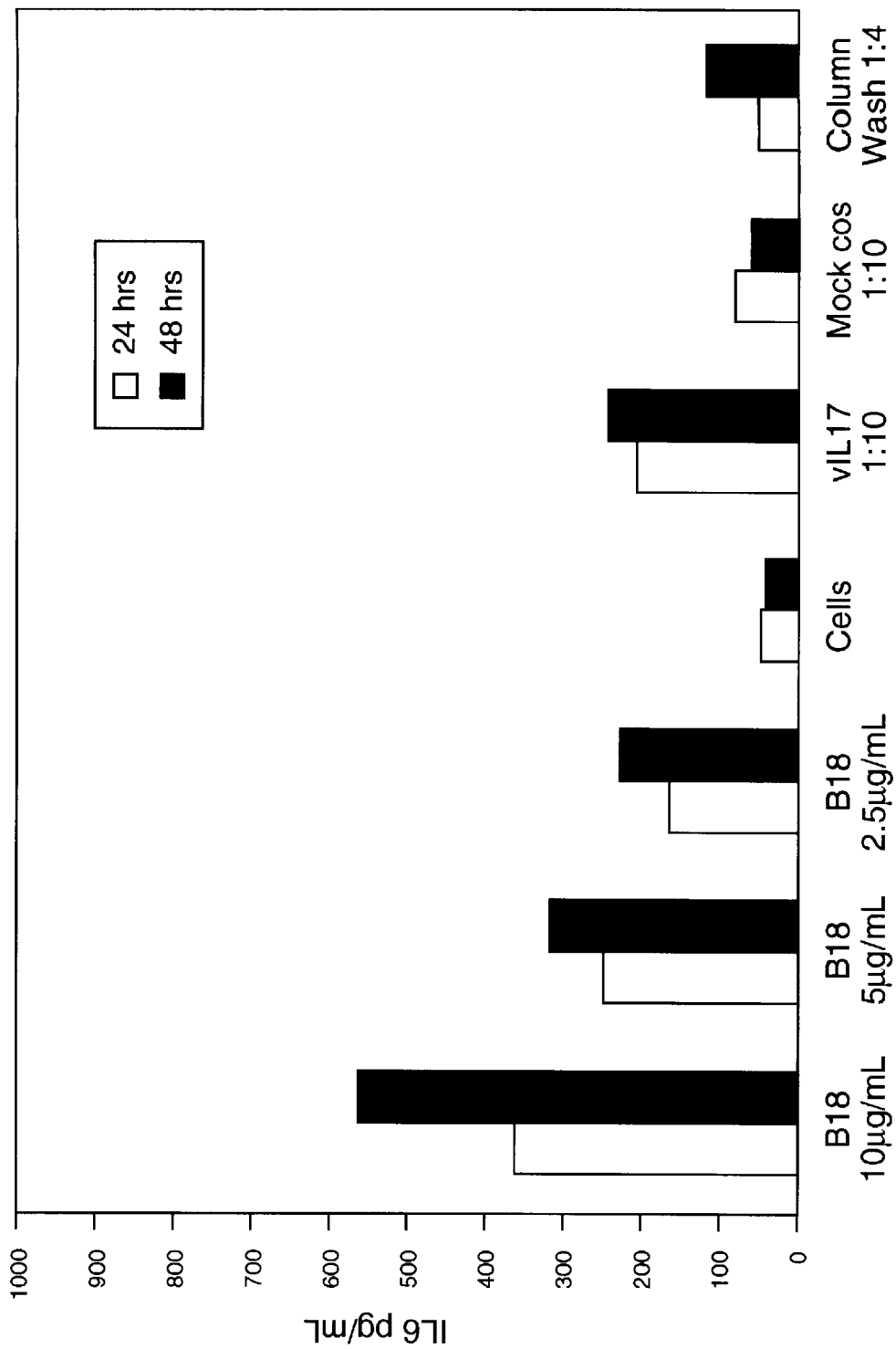
FIGS. 6 and 7 present data demonstrating the ability of human CILA-8 to induce production of L-6 and L-8.
Figure 7:
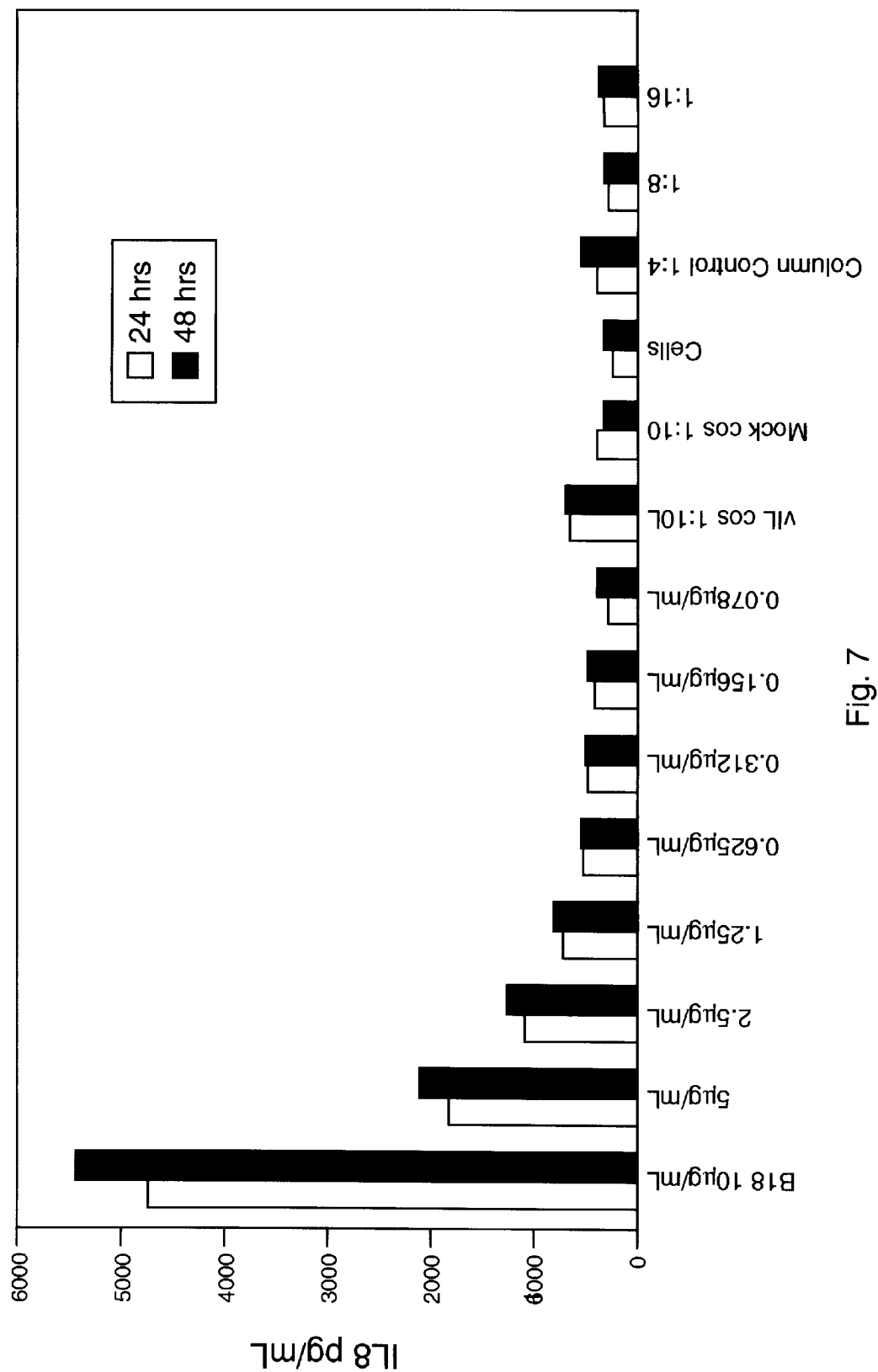

MRC5 cells were incubated in the presence of human CTLA-8 (B18) and production of IL-6 and IL-8 were measured. Herpes CTLA-8 (IL-17) was used as a positive control. Applicants' human CTLA-8 (B18) demonstrated titratable production of both IL-6 and IL-8 (see FIGS. 6 and 7).

All patent and literature references cited herein are incorporated by reference as if fully set forth.

What is claimed is:

1. An isolated human CTLA-8 protein comprising an amino acid sequence selected from the group consisting of:
   (a) the amino acid of SEQ ID NO:2;
   (b) the amino acid sequence of SEQ ID NO:2 from amino acids 11 to 163;
   (c) the amino acid sequence of SEQ ID NO:2 from amino acids 29 to 163;
   (d) the amino acid sequence of SEQ ID NO:2 from amino acids 31 to 163;
   (e) a fragment of SEQ ID NO:2, the fragment comprising amino acids 11–163 of SEQ ID NO:2;
   (f) a fragment of SEQ ID NO:2, and the fragment comprising amino acids 29–163 of SEQ ID NO:2;
   (g) a fragment of SEQ ID NO:2, the fragment comprising amino acids 31–163 of SEQ ID NO:2.

2. The protein of claim 1 comprising the amino acid sequence of SEQ ID NO:2.

3. The protein of claim 1 comprising the sequence from amino acid 29 to 163 of SEQ ID NO:2.

4. The protein of claim 1 comprising the sequence from amino acid 11 to 163 of SEQ ID NO:2.

5. The protein of claim 1 comprising a fragment of SEQ ID NO:2, the fragment comprising amino acids 11–163 of SEQ ID NO:2.

6. The protein of claim 1 comprising a fragment of SEQ ID NO:2, the fragment comprising amino acids 29–163 of SEQ ID NO:2.

7. The protein of claim 1 comprising a fragment of SEQ ID NO:2, the fragment comprising amino acids 31–163 of SEQ ID NO:2.

8. A human CTLA-8 protein produced according to a process which comprises the steps of:
(a) growing a culture of a cell in a suitable culture medium, wherein the cell is transformed with a polynucleotide operably linked to an expression control sequence, wherein the polynucleotide is selected from the group consisting of:
(aa) a polynucleotide comprising the nucleotide sequence of SEQ ID NO:1 from nucleotide 55 to nucleotide 544;
(ab) a polynucleotide comprising the nucleotide sequence of SEQ ID NO:1 from nucleotide 146 to nucleotide 544;
(ac) a polynucleotide comprising the nucleotide sequence of the full-length protein coding sequence of clone B18 deposited under accession number ATCC 69868;
(ad) a polynucleotide encoding the fill length protein encoded by the cDNA insert of clone B18 deposited under accession number ATCC 69868; and
(ae) a polynucleotide comprising a nucleotide sequence varying from the sequence of the nucleotide sequence specified in (aa)–(ad) as a result of degeneracy of the genetic code; and
(b) purifying the human CTLA-8 protein encoded by said polynucleotide from the culture.

9. The human CTLA-8 protein of claim 8, wherein said polynucleotide comprises the nucleotide sequence of SEQ ID NO:1 from nucleotide 55 to nucleotide 544.

10. The human CTLA-8 protein of claim 8 wherein said polynucleotide comprises the nucleotide sequence of SEQ ID NO:1 from nucleotide 146 to nucleotide 544.

11. The human CTLA-8 protein of claim 8, wherein said polynucleotide comprises the nucleotide sequence of the full-length protein coding sequence of clone B18 deposited under accession number ATCC 69868.

12. The human CTLA-8 protein of claim 8, wherein said polynucleotide comprises a polynucleotide encoding the full length protein encoded by the cDNA insert of clone B18 deposited under accession number ATCC 69868.

13. A pharmaceutical composition comprising a human CTLA-8 protein of claim 1 and a pharmaceutically acceptable carrier.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 813 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 56..544

(xi) SEQUENCE DESCRIPTION: SEQ ID NO:1:

```
GGGAAGATAC ATTCACAGAA AGAGCTTCCT GCACAAAGTA AGCCACCAGC GCAAC ATG       58
                                                              Met
                                                                1

ACA GTG AAG ACC CTG CAT GGC CCA GCC ATG GTC AAG TAC TTG CTG CTG      106
Thr Val Lys Thr Leu His Gly Pro Ala Met Val Lys Tyr Leu Leu Leu
          5                  10                  15

TCG ATA TTG GGG CTT GCC TTT CTG AGT GAG GCG GCA GCT CGG AAA ATC      154
Ser Ile Leu Gly Leu Ala Phe Leu Ser Glu Ala Ala Ala Arg Lys Ile
         20                  25                  30

CCC AAA GTA GGA CAT ACT TTT TTC CAA AAG CCT GAG AGT TGC CCG CCT      202
Pro Lys Val Gly His Thr Phe Phe Gln Lys Pro Glu Ser Cys Pro Pro
     35                  40                  45

GTG CCA GGA GGT AGT ATG AAG CTT GAC ATT GGC ATC ATC AAT GAA AAC      250
Val Pro Gly Gly Ser Met Lys Leu Asp Ile Gly Ile Ile Asn Glu Asn
 50                  55                  60                  65

CAG CGC GTT TCC ATG TCA CGT AAC ATC GAG AGC CGC TCC ACC TCC CCC      298
Gln Arg Val Ser Met Ser Arg Asn Ile Glu Ser Arg Ser Thr Ser Pro
                 70                  75                  80

TGG AAT TAC ACT GTC ACT TGG GAC CCC AAC CGG TAC CCC TCG GAA GTT      346
Trp Asn Tyr Thr Val Thr Trp Asp Pro Asn Arg Tyr Pro Ser Glu Val
             85                  90                  95

GTA CAG GCC CAG TGT AGG AAC TTG GGC TGC ATC AAT GCT CAA GGA AAG      394
Val Gln Ala Gln Cys Arg Asn Leu Gly Cys Ile Asn Ala Gln Gly Lys
            100                 105                 110

GAA GAC ATC TCC ATG AAT TCC GTT CCC ATC CAG CAA GAG ACC CTG GTC      442
Glu Asp Ile Ser Met Asn Ser Val Pro Ile Gln Gln Glu Thr Leu Val
        115                 120                 125

GTC CGG AGG AAG CAC CAA GGC TGC TCT GTT TCT TTC CAG TTG GAG AAG      490
Val Arg Arg Lys His Gln Gly Cys Ser Val Ser Phe Gln Leu Glu Lys
130                 135                 140                 145

GTG CTG GTG ACT GTT GGC TGC ACC TGC GTC ACC CCT GTC ATC CAC CAT      538
Val Leu Val Thr Val Gly Cys Thr Cys Val Thr Pro Val Ile His His
                150                 155                 160

GTG CAG TAAGAGGTGC ATATCCACTC AGCTGAAGAA GCTGTAGAAA TGCCACTCCT       594
Val Gln
```

```
TACCCAGTGC TCTGCAACAA GTCCTGTCTG ACCCCCAATT CCCTCCACTT CACAGGACTC    654

TTAATAAGAC CTGCACGGAT GGAAACAGAA AATATTCACA ATGTATGTGT GTATGTACTA    714

CACTTTATAT TTGATATCTA AAATGTTAGG AGAAAAATTA ATATATTCAG TGCTAATATA    774

ATAAAGTATT AATAATTTAA AAATAAAAAA AAAAAAAAA                           813
```

(2) INFORMATION FOR SEQ ID NO:2:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Val Lys Thr Leu His Gly Pro Ala Met Val Lys Tyr Leu Leu
 1               5                  10                  15

Leu Ser Ile Leu Gly Leu Ala Phe Leu Ser Glu Ala Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

His Val Gln
```

(2) INFORMATION FOR SEQ ID NO:3:

(i) SEQUENCE CHARACTERISTICS:
        (A) LENGTH: 461 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 6..455

(xi) SEQUENCE DESCRIPTION: SEQ ID NO:3:

```
CCACC ATG TGC CTG ATG CTG TTG CTG CTA CTG AAC CTG GAG GCT ACA         47
      Met Cys Leu Met Leu Leu Leu Leu Leu Asn Leu Glu Ala Thr
       1               5                  10

GTG AAG GCA GCG GTA CTC ATC CCT CAA AGT TCA GTG TGT CCA AAC GCC       95
Val Lys Ala Ala Val Leu Ile Pro Gln Ser Ser Val Cys Pro Asn Ala
 15                  20                  25                  30
```

```
GAG GCC AAT AAC TTT CTC CAG AAC GTG AAG GTC AAC CTG AAA GTC ATC         143
Glu Ala Asn Asn Phe Leu Gln Asn Val Lys Val Asn Leu Lys Val Ile
                 35                  40                  45

AAC TCC CTT AGC TCA AAA GCG AGC TCG AGA AGG CCC TCA GAT TAC CTC         191
Asn Ser Leu Ser Ser Lys Ala Ser Ser Arg Arg Pro Ser Asp Tyr Leu
             50                  55                  60

AAC CGT TCC ACT TCA CCC TGG ACT CTG AGC CGC AAT GAG GAC CCT GAT         239
Asn Arg Ser Thr Ser Pro Trp Thr Leu Ser Arg Asn Glu Asp Pro Asp
                 65                  70                  75

AGA TAT CCT TCT GTG ATC TGG GAG GCA CAG TGC CGC CAC CAG CGC TGT         287
Arg Tyr Pro Ser Val Ile Trp Glu Ala Gln Cys Arg His Gln Arg Cys
         80                  85                  90

GTC AAC GCT GAG GGG AAG TTG GAC CAC CAC ATG AAT TCT GTT CTC ATC         335
Val Asn Ala Glu Gly Lys Leu Asp His His Met Asn Ser Val Leu Ile
 95                 100                 105                 110

CAG CAA GAG ATA CTA GTC CTG AAG AGG GAG CCT GAG AAG TGC CCC TTC         383
Gln Gln Glu Ile Leu Val Leu Lys Arg Glu Pro Glu Lys Cys Pro Phe
                115                 120                 125

ACT TTC CGG GTG GAG AAG ATG CTG GTG GGC GTG GGC TGC ACC TGC GTT         431
Thr Phe Arg Val Glu Lys Met Leu Val Gly Val Gly Cys Thr Cys Val
            130                 135                 140

TCC TCT ATT GTC CGC CAT GCG TCC TAATAA                                  461
Ser Ser Ile Val Arg His Ala Ser
            145                 150

(2) INFORMATION FOR SEQ ID NO:4:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:4:

Met Cys Leu Met Leu Leu Leu Leu Asn Leu Glu Ala Thr Val Lys
 1               5                  10                  15

Ala Ala Val Leu Ile Pro Gln Ser Ser Val Cys Pro Asn Ala Glu Ala
            20                  25                  30

Asn Asn Phe Leu Gln Asn Val Lys Val Asn Leu Lys Val Ile Asn Ser
         35                  40                  45

Leu Ser Ser Lys Ala Ser Ser Arg Arg Pro Ser Asp Tyr Leu Asn Arg
     50                  55                  60

Ser Thr Ser Pro Trp Thr Leu Ser Arg Asn Glu Asp Pro Asp Arg Tyr
 65                  70                  75                  80

Pro Ser Val Ile Trp Glu Ala Gln Cys Arg His Gln Arg Cys Val Asn
                 85                  90                  95

Ala Glu Gly Lys Leu Asp His His Met Asn Ser Val Leu Ile Gln Gln
            100                 105                 110

Glu Ile Leu Val Leu Lys Arg Glu Pro Glu Lys Cys Pro Phe Thr Phe
        115                 120                 125

Arg Val Glu Lys Met Leu Val Gly Val Gly Cys Thr Cys Val Ser Ser
    130                 135                 140

Ile Val Arg His Ala Ser
145                 150

(2) INFORMATION FOR SEQ ID NO:5:

(i) SEQUENCE CHARACTERISTICS:
        (A) LENGTH: 459 base pairs
```

(B) TYPE: nucleic acid
    (C) STRANDEDNESS: double
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 1..453

(xi) SEQUENCE DESCRIPTION: SEQ ID NO:5:

```
ATG ACA TTT AGA ATG ACT TCA CTT GTG TTA CTT CTG CTG CTG AGC ATA      48
Met Thr Phe Arg Met Thr Ser Leu Val Leu Leu Leu Leu Leu Ser Ile
 1               5                  10                  15

GAT TGT ATA GTA AAG TCA GAA ATA ACT AGT GCA CAA ACC CCA AGA TGC      96
Asp Cys Ile Val Lys Ser Glu Ile Thr Ser Ala Gln Thr Pro Arg Cys
             20                  25                  30

TTA GCT GCT AAC AAT AGC TTT CCA CGG TCT GTG ATG GTT ACT TTG AGC     144
Leu Ala Ala Asn Asn Ser Phe Pro Arg Ser Val Met Val Thr Leu Ser
         35                  40                  45

ATC CGT AAC TGG AAT ACC AGT TCT AAA AGG GCT TCA GAC TAC TAC AAT     192
Ile Arg Asn Trp Asn Thr Ser Ser Lys Arg Ala Ser Asp Tyr Tyr Asn
     50                  55                  60

AGA TCT ACG TCT CCT TGG ACT CTC CAT CGC AAT GAA GAT CAA GAT AGA     240
Arg Ser Thr Ser Pro Trp Thr Leu His Arg Asn Glu Asp Gln Asp Arg
 65                  70                  75                  80

TAT CCC TCT GTG ATT TGG GAA GCA AAG TGT CGC TAC TTA GGA TGT GTT     288
Tyr Pro Ser Val Ile Trp Glu Ala Lys Cys Arg Tyr Leu Gly Cys Val
                 85                  90                  95

AAT GCT GAT GGG AAT GTA GAC TAC CAC ATG AAC TCA GTC CCT ATC CAA     336
Asn Ala Asp Gly Asn Val Asp Tyr His Met Asn Ser Val Pro Ile Gln
            100                 105                 110

CAA GAG ATT CTA GTG GTG CGC AAA GGG CAT CAA CCC TGC CCT AAT TCA     384
Gln Glu Ile Leu Val Val Arg Lys Gly His Gln Pro Cys Pro Asn Ser
        115                 120                 125

TTT AGG CTA GAG AAG ATG CTA GTG ACT GTA GGC TGC ACA TGC GTT ACT     432
Phe Arg Leu Glu Lys Met Leu Val Thr Val Gly Cys Thr Cys Val Thr
    130                 135                 140

CCC ATT GTT CAC AAT GTA GAC TAAAAG                                  459
Pro Ile Val His Asn Val Asp
145                 150
```

(2) INFORMATION FOR SEQ ID NO:6:

(i) SEQUENCE CHARACTERISTICS:
    (A) LENGTH: 151 amino acids
    (B) TYPE: amino acid
    (D) TOPOLOGY: linear (ii) MOLECULE TYPE: protein (xi) SEQUENCE DESCRIPTION: SEQ ID NO:6:

```
Met Thr Phe Arg Met Thr Ser Leu Val Leu Leu Leu Leu Leu Ser Ile
 1               5                  10                  15

Asp Cys Ile Val Lys Ser Glu Ile Thr Ser Ala Gln Thr Pro Arg Cys
             20                  25                  30

Leu Ala Ala Asn Asn Ser Phe Pro Arg Ser Val Met Val Thr Leu Ser
         35                  40                  45

Ile Arg Asn Trp Asn Thr Ser Ser Lys Arg Ala Ser Asp Tyr Tyr Asn
     50                  55                  60

Arg Ser Thr Ser Pro Trp Thr Leu His Arg Asn Glu Asp Gln Asp Arg
```

-continued

```
                65                  70                  75                  80
     Tyr Pro Ser Val Ile Trp Glu Ala Lys Cys Arg Tyr Leu Gly Cys Val
                            85                  90                  95

Asn Ala Asp Gly Asn Val Asp Tyr His Met Asn Ser Val Pro Ile Gln
                    100                 105                 110

Gln Glu Ile Leu Val Val Arg Lys Gly His Gln Pro Cys Pro Asn Ser
                115                 120                 125

Phe Arg Leu Glu Lys Met Leu Val Thr Val Gly Cys Thr Cys Val Thr
            130                 135                 140

Pro Ile Val His Asn Val Asp
     145                 150
```

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:7:

CACAGGCATA CACAGGAAGA TACATTCA                       28

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:8:

TCTTGCTGGA TGGGAACGGA ATTCA                          25

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:9:

ATACATTCAC AGAAGAGCTT CCTGCACA                       28